(12) United States Patent
Zamora et al.

(10) Patent No.: US 6,931,916 B2
(45) Date of Patent: Aug. 23, 2005

(54) VISCOMETER SAG TEST SHOE

(75) Inventors: Mario Zamora, Houston, TX (US); Marian Baranowski, Houston, TX (US)

(73) Assignee: M-I L.L.C., Houston, TX (US)

( * ) Notice: Subject to any disclaimer, the term of this patent is extended or adjusted under 35 U.S.C. 154(b) by 40 days.

(21) Appl. No.: 10/603,849

(22) Filed: Jun. 25, 2003

(65) Prior Publication Data

US 2004/0261507 A1 Dec. 30, 2004

(51) Int. Cl.$^7$ .............................................. G01N 15/04
(52) U.S. Cl. .................. 73/61.63; 73/54.28; 73/54.37; 73/152.62; 210/711
(58) Field of Search ............................ 73/61.63, 54.28, 73/54.37, 152.62; 210/711

(56) References Cited

U.S. PATENT DOCUMENTS

| | | | |
|---|---|---|---|
| 4,076,620 A | * 2/1978 | Opferkuch et al. | 210/711 |
| 6,330,826 B1 | 12/2001 | Meeten | 73/152.62 |
| 6,584,833 B1 | 7/2003 | Jamison et al. | 73/61.63 |

OTHER PUBLICATIONS

D. T. Jefferson; *New Procedure Helps Monitor Sag in the Field*; The American Society of Mechanical Engineers; Jan. 20–24, 1991; (pp. 1–7).

SPE 20423; P. M. Hanson, et al; *Investigation of Barite "Sag" In Weighted Drilling Fluids in Highly Deviated Wells*; Sep. 22–26–1990; (pp. 223–230).

SPE 36670; P. A. Berm, et al; *The Influence of Drilling Variables on Barite Sag*; Oct. 6–9 1996; (pp. 1–8).

IADC/SPE 47784; P. A. Berm, et al; *Barite Sag: Measurement, Modelling and Management*; Sep. 7–9 1998; (pp. 89–97).

Barite Sag; Chapter 20A; *M=I Viscometer Sag Test (VST)*; Dated Mar. 31, 1998; (pp. 20A.6–20A–11).

Mario Zamora, et al; *Controlling Barite Sag Can Reduce Drilling Problems*; Oil & Gas Journal; Feb. 14, 1994 OGJ Special; (pp. 47–52).

* cited by examiner

*Primary Examiner*—Hezron Williams
*Assistant Examiner*—André K. Jackson
(74) *Attorney, Agent, or Firm*—Osha·Liang L.L.P.

(57) ABSTRACT

Methods and apparatus for measuring sag properties of a drilling fluid using a rotary viscometer. An insert, or shoe, is placed at the bottom of the heat cup containing the fluid to be tested. A rotating cylinder is disposed within the fluid and solid particles are allowed to settle toward the bottom of the heat cup. The shoe incorporates a curved and inclined upper surface that directs the settled particles toward a well non-centrally located in the shoe. As the test is performed, fluid samples can be withdrawn from the well and analyzed. The samples can then be returned to the well and the test continued. The insert concentrates the settled solids into a single location, which increases the sensitivity of the test and provides a location for sample acquisition that is easily and repeatedly located, which allows for improved correlation with laboratory and flow loop results.

9 Claims, 3 Drawing Sheets

VISCOMETER SAG TEST SHOE

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD OF THE INVENTION

The present invention relates generally to methods and apparatus used in the testing of fluids. More specifically, the present invention relates to methods and apparatus used to test the settling characteristics of solid particles within a fluid. Still more specifically, the present invention relates to methods and apparatus for monitoring barite sag in drilling fluids.

BACKGROUND OF THE INVENTION

Rotary drilling techniques are used extensively in drilling hydrocarbon wells, water wells, and mining applications. In rotary drilling, a fluid, commonly known as drilling mud, is circulated down a drill string, through a drill bit, and back up the borehole to the surface. The drilling mud acts as a lubricant for the drill bit and carries cuttings from the bottom of the borehole to the surface.

Most rotary drilling applications also rely on the drilling mud to control underground pressures developed by the formation fluids. Therefore, the density of the drilling mud is closely maintained in order to control the hydrostatic pressure that the mud exerts at the bottom of the well. If the mud is too light, formation fluids, which are at higher pressures than the hydrostatic pressure developed by the drilling mud, can enter the wellbore and flow uncontrolled to the surface, possibly causing a blowout. If the mud is too heavy, then the hydrostatic pressure exerted at the bottom of the wellbore can reduce the rate at which the drill bit will drill the hole.

Thus, the control of the solids content of the drilling fluid is very crucial to the overall efficiency and safe operation of the rig. In the most common applications, the density of the drilling mud is increased by adding a particulate weighting agent, such as barite. These particles are prone to settling within the drilling mud under the influence of gravity. This settling is known in the industry as "sag" or "barite sag" and is a persistent and potentially serious drilling problem that occurs most prevalently in directional wells drilled with weighted drilling muds.

This complex phenomenon involves dynamic and static settling of weight material, followed by downward slumping of the fluidized beds that form on the low side of the inclined wellbore. The existence of these high-density beds, and their subsequent recirculation, can lead to severe operational problems, including well-control issues, lost circulation, wellbore instability, and stuck pipe.

Barite sag was once thought to be caused by the inability of mud to properly suspend weight material in an inclined wellbore under static conditions. Laboratory tests to evaluate mud sag tendency were limited to static tests in inclined tubes. However, a 1990 landmark paper by Hanson, et. al. (SPE 20423 "Investigation of Barite Sag in Weighted Drilling Fluids in Highly Deviated Wells," which is incorporated herein by reference for all purposes) concluded that sag was primarily a dynamic settling problem, which was subsequently supported by laboratory flow loop tests correlated to field data.

For maximum effort to mitigate problems, mud sag tendencies should be measured and monitored under dynamic conditions at the wellsite. Several direct-measurement field tests have been proposed; however, most have been variations on a VST ("Viscometer Sag Test") procedure introduced in 1991 in a technical paper by D. T. Jefferson (91-PET-3 "New Procedure Helps Monitor Sag in the Field", presented at the ASME Energy-Resources Technology Conference and Exhibition, New Orleans, La., Jan. 20–24, 1991), which is incorporated herein by reference for all purposes.

The VST procedure involves a standard, concentric-cylinder, field viscometer, which provides the dynamic flow conditions, and an API mud heat cup which acts both as a container and a heat source. A syringe is used to extract mud samples (approximately 10 ml) from the bottom of the heat cup at the beginning and end of a 30-minute test. Different techniques have been used to measure the density of the samples, including (a) a 10-ml retort cup and digital scale, (b) the sampling syringe and digital scale, and (c) a small-volume "pocket" mud balance. The sag tendency of a particular fluid is considered to be proportional to the density difference between the samples taken at the beginning and end of the test.

Key elements of the VST include the following: (a) it is a direct density measurement, (b) the mud sample is dynamic, (c) the mud sample is maintained at an elevated, controlled temperature, (d) it uses existing and/or common field test equipment, and (e) the shear history of the mud sample is consistent. One of the drawbacks of the conventional VST test is that the particles are allowed to settle naturally to the bottom of the cup. The distribution of the particles at the bottom is unpredictable and there is no guarantee that the sample will be taken in an area of representative concentration. Further, there is no way to verify that each sample is collected from the same point in the cup every time. This has resulted in a lack of consistency of results or repeatability in the testing, especially when performed by different operators. Because of these inconsistencies, conventional VST results have not been convincingly correlated to laboratory flow loop or field results.

Thus, there remains a need in the art for consistent, repeatable, and practical methods and apparatus for field testing drilling mud, and other weighted fluids, to determine sag propensity. Therefore, the embodiments of the present invention are directed to methods and apparatus for testing drilling mud, and other weighted fluids, that seek to overcome these and other limitations of the prior art.

SUMMARY OF THE PREFERRED EMBODIMENTS

Accordingly, there are provided herein methods and apparatus for measuring sag properties of a drilling fluid using a rotary viscometer. An insert, or shoe, is placed at the bottom of the heat cup containing the fluid to be tested. A rotating cylinder is disposed within the fluid and solid particles are allowed to settle toward the bottom of the heat cup. The shoe incorporates a curved and inclined upper surface that directs the settled particles toward a well located at or near the outer edge of the shoe. As the test is performed, fluid samples can be withdrawn from the well and analyzed. If appropriate, the samples can then be returned to the well and the test continued. The insert concentrates the settled solids into a single location, which increases the sensitivity of the test and provides a location for sample acquisition that is easily and repeatedly located, which allows for improved correlation with laboratory and flow loop results.

In one embodiment, an assembly for testing the settling characteristics of a fluid containing solid particles comprises a cup and a cylinder disposed within the cup forming an annulus between the cylinder and the cup. The cup includes a well at the bottom and disposed proximate to the wall of the cup and a surface adapted to urge the solid particles into the well as they settle within the fluid. The surface may be inclined and/or curved. In certain embodiments, the surface comprises a first surface, which is curved about a first axis that is inclined toward the well, and a second surface, which is curved about a second axis that is inclined toward the well. The second surface is lower and steeper than the first surface creating a lip formed at the junction of the surfaces. In the preferred embodiments, the surface and the well are formed within an insert removably disposed in the cup.

In an alternate embodiment, the testing assembly comprises a cup with a cylindrical body, an open top, and a flat bottom. A rotating cylinder is disposed within the cup and forms an annular area between the cylinder and the cup. An insert is disposed at the bottom of the cup and includes a well proximate to the outer edge of the insert and an upper surface adapted to direct settling particles toward the well. In certain embodiments, the upper surface of the insert is curved and inclined and comprises a first curved surface and a second curved surface, wherein the second curved surface is lower and steeper than the first curved surface and the intersection between the first and second surfaces forms a lip. The first curved surface and the second curved surface each have a central axis inclined toward the well.

In another embodiment, a method for evaluating the settling characteristics of a fluid containing solid particles comprises: disposing the fluid within a cup, extracting a first sample of fluid from a well at the bottom of the cup in a position proximate to the wall of the cup, wherein the well is accessed through the annulus formed between the rotating cylindrical body and the cup, rotating a cylindrical body within the fluid for a selected time period, extracting a second sample of fluid from the well, and comparing a measured property of the second sample to a measured property of the first sample. The method may also include returning the second sample to the well, rotating the cylindrical body within the fluid for a selected time period, extracting a third sample of fluid from the well, and comparing a measured property of the third sample to the measured properties of the second sample and the first sample. The rotational speed of the cylindrical body may be increased between the second and third samples.

Thus, the present invention comprises a combination of features and advantages that enable it to improve the consistency, sensitivity, and accuracy of viscometer sag test results. These and various other characteristics and advantages of the present invention will be readily apparent to those skilled in the art upon reading the following detailed description of the preferred embodiments of the invention and by referring to the accompanying drawings.

BRIEF DESCRIPTION OF THE DRAWINGS

For a more detailed understanding of the preferred embodiments, reference is made to the accompanying Figures, wherein.

DETAILED DESCRIPTION OF THE PREFERRED EMBODIMENTS

Figure 1:
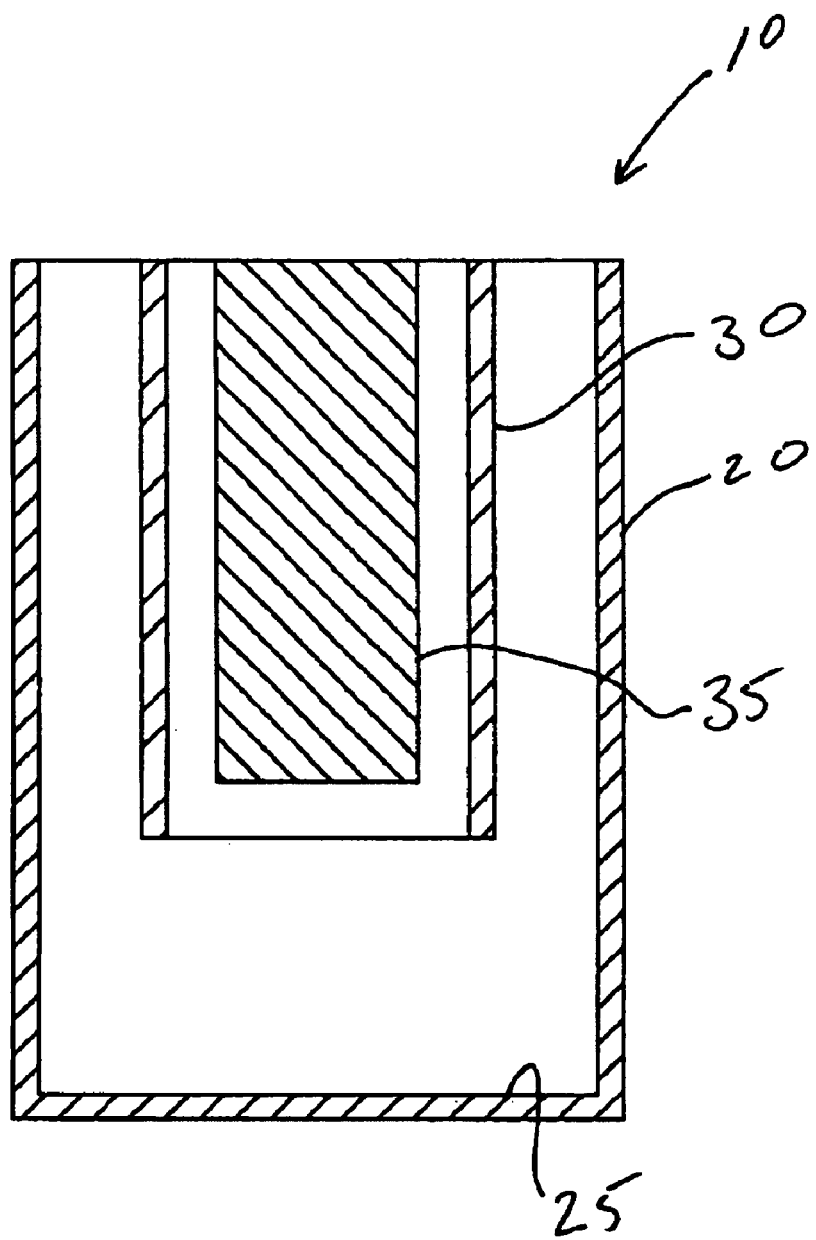
FIG. 1 is a sectional view of a standard VST testing apparatus.

In the description that follows, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness.

The preferred embodiments of the present invention relate to methods and apparatus for testing settling characteristics of a weight material in a fluid. The present invention is susceptible to embodiments of different forms. There are shown in the drawings, and herein will be described in detail, specific embodiments of the present invention with the understanding that the present disclosure is to be considered an exemplification of the principles of the invention, and is not intended to limit the invention to that illustrated and described herein.

In particular, various embodiments of the present invention provide a number of different methods and apparatus for evaluating barite sag characteristics of a drilling fluid. Reference is made to the application of the concepts of the present invention to the evaluation of drilling fluids, but the use of the concepts of the present invention is not limited to these applications, and can be used for any other application evaluating particulate fluids or slurries, such as production, completion, servicing, or injection fluids. It is to be fully recognized that the different teachings of the embodiments discussed below may be employed separately or in any suitable combination to produce desired results.

FIG. 1 is sectional schematic representation of a standard viscometer sag test (VST) assembly 10. The VST assembly 10 includes a heat cup 20 with a flat bottom 25, a rotating cylinder 30, and a stationary cylinder 35. Drilling fluid is placed in heat cup 20 and rotating cylinder 30 is rotated at a selected speed. During the test, samples are extracted from the bottom of heat cup 20 using a long syringe inserted at the top of the cup through the annulus between rotating cylinder 30 and the wall of heat cup 20. The density of the samples are determined and compared to evaluate the settling characteristics of the fluid. A full explanation of the standard VST test procedure can be found in the previously incorporated reference by D. T. Jefferson titled "New Procedure Helps Monitor Sag in the Field."

The preferred embodiments seek to improve the standard VST test by placing a non-reactive insert, or shoe, in the bottom of heat cup 20 before running the otherwise standard VST procedure. Alternatively, the insert, or shoe, can be integral with heat cup 20. Additionally, those skilled in the art will understand that, while a conventional heat cup 20 is a standard piece of equipment and therefore part of the preferred embodiments, other acceptable containers can be used in conjunction with the insert or shoe. The primary purposes of the insert include improving the consistency, sensitivity, and accuracy of the results. These improvements, which will be discussed in detail, are achieved by providing sufficient slope on the top surface of the shoe to accelerate settling and concentrate the settled weight material into a single location at the bottom of heat cup 20.

The single concentration of material provides a location from which a sample can be consistently and repeatedly acquired. This single location, which can be positively located while taking a sample, also permits the sample to be returned to the cup in the same location. This allows for multiple samples to be taken during a single test. Returning the sample, to the same location from which it was collected, also permits a continuation of the test at a higher rotation rate, which can be used to measure the relative capability of the fluid to pick up settled particles.

Figure 2:
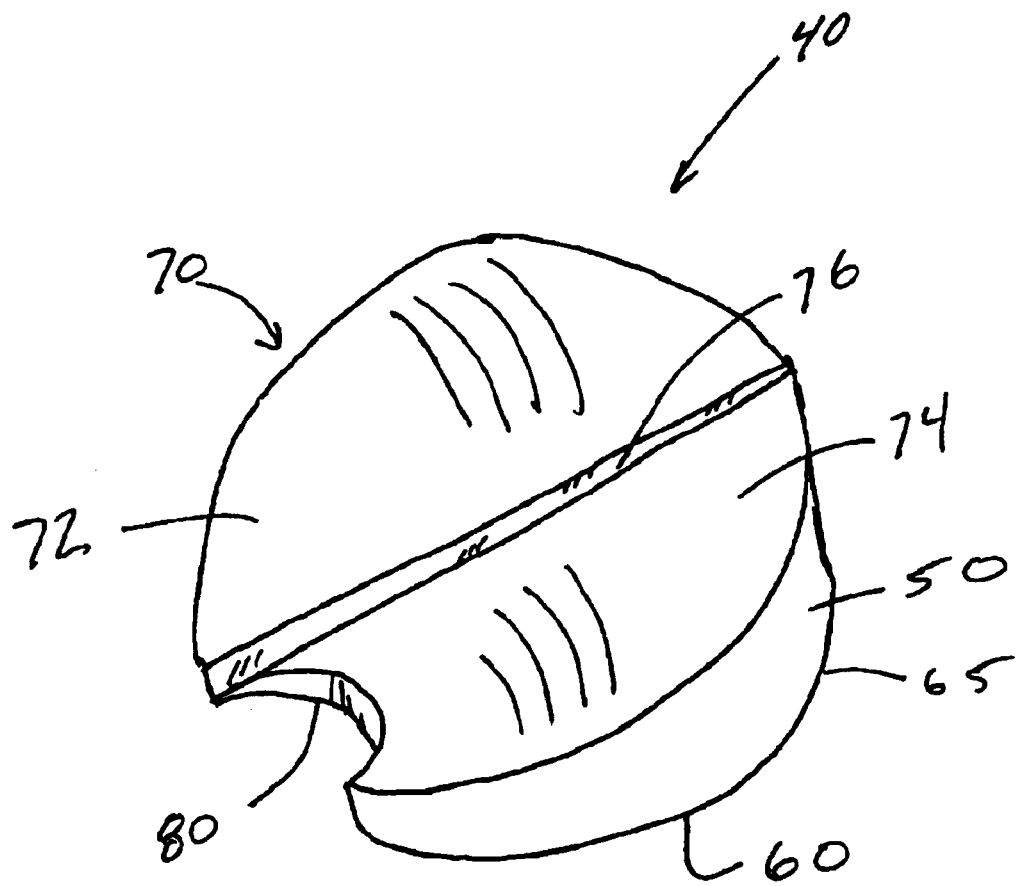
FIG. 2 is an isometric view of one embodiment of a VST shoe.

Referring now to FIG. 2, one embodiment of a shoe 40 is shown. Shoe 40 is formed from a disc 50 having a substantially flat base 60 and a diameter 65 suited for easy engagement with the inside of heat cup 20. Shoe 40 further comprises an upper surface 70 that is shaped to direct settling particles toward a well 80 near the edge of disc 50. It is understood that many geometrical shapes and combinations of shapes for upper surface 70 and well 80 may be used to create the advantages provided by the embodiments of the current invention.

In the embodiment shown in FIG. 2, upper surface 70 includes a first surface 72 and a second surface 74, which is slightly lower and steeper than the first surface. Both first surface 72 and second surface 74 are preferably cylindrical surfaces with axes crossing a point near the center of disc 50. Additionally, the first and second surfaces 72, 74 are preferably inclined toward well 80, such that the surfaces curve and slope toward well 80. The intersection between first surface 72 and second surface 74 forms a lip 76 that increases in height as the lip approaches well 80.

Well 80 serves as a collection point for solid particles that settle within heat cup 20. Well 80 is preferably non-centrally located within heat cup 20 such that the well can be accessed by a needle extended through the annulus between rotating cylinder 30 and heat cup 20. Thus, well 80 provides a verifiable location that can be accessed from the top of heat cup 20 using standard sample acquisition techniques, e.g., a long needle inserted in the top of the heat cup. In order to collect the most solid particles and be easily located, well 80 preferably is located at or includes the lowest point within heat cup 20 and is proximate to the wall of the heat cup.

The physical dimensions of shoe 40 are controlled by the geometry of the particular viscometer and heat cup used in a given test assembly. The preferred diameter of disc 50 is the maximum size that still permits easy entry in and removal from a standard-sized heat cup, or about 2.35 in. The overall slope of upper surface 70 is preferably the practical maximum that will not interfere with normal viscometer operation, for example about 3/16-in high on the well side and nearly 1-in high on the opposite side. A constant distance, such as approximately 7 mm, is preferably maintained between the bottom of the rotating cylinder 30 and the top of shoe 40 by adjusting the depth of cylinder 30. The preferred diameter of well 80 is approximately 3/4-in.

Shoe 40 is preferably constructed from a material that can be easily machined, molded, or cast into complex shapes. The preferred material should also handle test temperatures to 180° F. and be resistant to all water-based, oil-based and synthetic-based muds. An acetal thermoplastic is one example of a suitable material.

Figure 3:
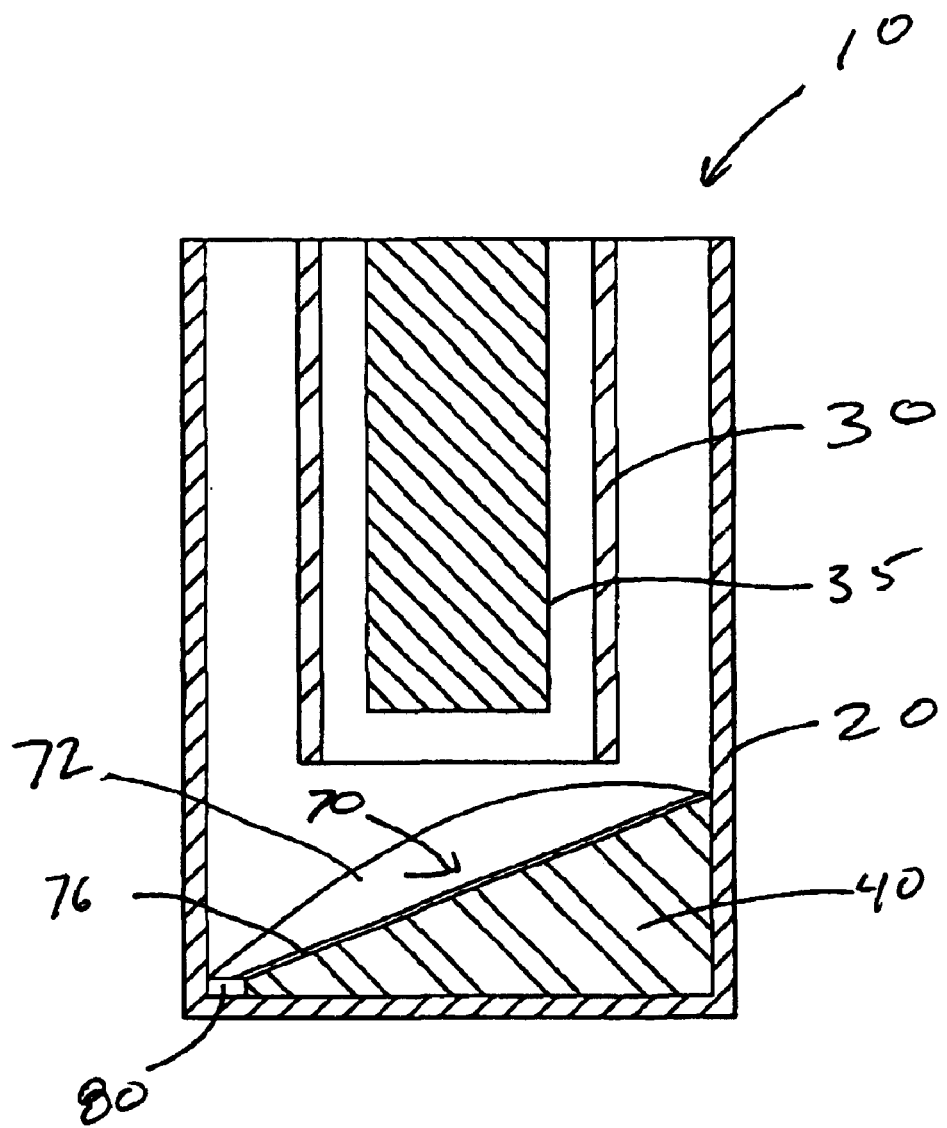
FIG. 3 is a sectional view of a VST shoe installed in a standard testing apparatus.

Referring now to FIG. 3, shoe 40 is shown installed in VST assembly 10. As the test is conducted, the sloped, curved upper surface 70 facilitates settling and concentration of weight material into well 80. This concentration of material increases the sensitivity of the test. Well 80 also provides a location for sample acquisition that can be easily detected by the tip of a syringe in order to ensure that samples are extracted from and returned to the same location. The ability to return a sample allows for multiple data points to be taken during the test procedure. Lip 76, caused by the misaligned surfaces 72 and 74, helps prevent settled particles from being recirculated during sag testing, but it is not too high to prevent bed pickup at higher viscometer rotary speeds.

The recommended test procedure with the shoe 40 is similar to the standard VST procedure described previously and known in the art, except that the procedure can now include steps to measure sag pick-up. For example, at the conclusion of the standard timed sag test, the test sample is replaced in well 80 using the syringe. The viscometer speed is then increased for a set period of time, such as 600 rpm for 20 min, after which another sample is extracted and weighed. A comparison of the three sample densities gives an indication of how easily the bed can be picked up by rotation.

The preferred embodiments can also help with correlation to sag flow loop data since well 80 permits easy and precise replacement of the extracted samples. Measurements, including sample returns, can be made at more frequent intervals, such as 5 or 10 min, and for longer time periods, thus permitting more precise evaluation of the rate at which the bed density increases or decreases by providing additional data points and a realistic continuing test.

The embodiments set forth herein are merely illustrative and do not limit the scope of the invention or the details therein. It will be appreciated that many other modifications and improvements to the disclosure herein may be made without departing from the scope of the invention or the inventive concepts herein disclosed. Because many varying and different embodiments may be made within the scope of the inventive concept herein taught, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An assembly for testing the settling characteristics of a fluid containing solid particles, said assembly comprising:
   a container adapted to contain the fluid; and
   a surface disposed within said container and adapted to urge the solid particles into a well as the solid particles settle within the fluid; wherein the well is non-centrally located within said container;
   wherein in said container comprises a cup that includes a cylindrical wall and the assembly further comprises a cylinder disposed within said cup forming an annulus between said cylinder and said cup, wherein the well is accessible through the annulus.

2. An assembly for testing the settling characteristics of a fluid containing solid particles, said assembly comprising:
   a container adapted to contain the fluid; and
   a surface disposed within said container and adapted to urge the solid particles into a well as the solid particles settle within the fluid; wherein the well is non-centrally located within said container, wherein the surface comprises:
   a first surface curved about a first axis that is inclined toward the well; and
   a second surface curved about a second axis that is inclined toward the well,
   wherein said second surface is lower and steeper than said first surface.

3. The assembly of claim 2 further comprising a lip formed at the junction of said first and second surfaces.

4. An assembly for testing the settling characteristics of a fluid containing solid particles, said assembly comprising:
- a container adapted to contain the fluid; and
- a surface disposed within said container and adapted to urge the solid particles into a well as the solid particles settle within the fluid; wherein the well is non-centrally located within said container;
- wherein said surface and said well are formed within an insert removably disposed in said container.

5. A testing assembly comprising:
- an insert disposed at the bottom of a cup containing a fluid having suspended solid particles;
- a well non-centrally located within said insert; and
- an upper surface disposed on said insert and adapted to direct settling particles toward said well, wherein said upper surface comprises a first curved surface and a second curved surface.
- wherein the second curved surface is lower and steeper than the first curved surface.

6. A testing assembly comprising:
- an insert disposed at the bottom of a cup containing a fluid having suspended solid particles;
- a well non-centrally located within said insert; and
- an upper surface disposed on said insert and adapted to direct settling particles toward said well, wherein said upper surface comprises a first curved surface and a second curved surface,
- wherein an intersection between the first and second surfaces forms a lip.

7. A method for evaluating the settling characteristics of a fluid containing solid particles, wherein said method comprises:
- disposing the fluid within a cup;
- extracting a first sample of fluid from a well in a non-centrally located position within the cup;
- rotating a cylindrical body within the fluid for a selected time period;
- extracting a second sample of fluid from the well, wherein the well is accessed through an annulus formed between the rotating cylindrical body and the cup; and
- comparing a measured property of the second sample to a measured property of the first sample.

8. The method of claim 7 further comprising:
- returning the second sample to the well;
- rotating the cylindrical body within the fluid for a selected time period;
- extracting a third sample of fluid from the well; and
- comparing a measured property of the third sample to the measured properties of the second sample and the first sample.

9. The method of claim 8 wherein between the second sample and the third sample the cylindrical body is rotated at a higher rate than between the first and second sample.

* * * * *